US00PP12291P2

(12) United States Plant Patent
Drewlow

(10) Patent No.: US PP12,291 P2
(45) Date of Patent: Dec. 18, 2001

(54) NEW GUINEA IMPATIENS PLANT NAMED 'OVATION PURPLE'

(75) Inventor: Lyndon W. Drewlow, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/550,509

(22) Filed: Apr. 17, 2000

(51) Int. Cl.[7] ..... A01H 5/00

(52) U.S. Cl. ..... Plt./318

(58) Field of Search ..... Plt./318

*Primary Examiner*—Bruce R. Campell
*Assistant Examiner*—Anne Marie Grünberg
(74) *Attorney, Agent, or Firm*—Webb Ziesenheim Logsdon Orkin & Hanson, P.C.

(57) ABSTRACT

A distinct cultivar of Impatiens plant named Ovation Purple, characterized by its deep red-purple flower color, large flower diameter, bright green leaves, continuous, and long-lasting flowering, self-branching and vigorous habit.

1 Drawing Sheet

The present invention relates to a new and distinctive cultivar of Impatiens plant, botanically known as *Impatiens hawkeri*, commercially known as New Guinea Impatiens, and known by the cultivar name 'Ovation Purple'. Ovation Purple was developed in a controlled breeding program by crossing Papete, U.S. Plant Pat. No. 8,457 (seed parent) with Mikkelsen Seedling No. 92-459-2 (pollen parent). The pollen parent is a proprietary breeding line which has not been sold or made publicly available in this country.

Asexual reproduction carried out by the inventor in Lompoc, Calif. by terminal or stem cuttings has shown that the unique features of this new Impatiens are stabilized and are reproduced true to type in successive propagations.

The following combination of characteristics distinguishes the new Impatiens from both its parent varieties and other cultivated Impatiens of this type known and used in the floriculture industry:

1. The flowers of Ovation Purple are similar in color (Red-Purple Group 74A) to Papete (U.S. Plant Pat. No. 8,457) and has a deeper purple color (74B) as compared to Harmony Grape (unpatented).

2. Ovation Purple has a larger flower diameter (7 to 7.5 cm) than either Papete or Harmony Grape (6 to 6.5 cm).

3. The underside of the leaves of Ovation Purple has a deep red-purple color to the midrib and veins while Papete and Harmony Grape have a much lighter red-purple cast.

4. Ovation Purple has bright green leaves while Harmony Grape has dull green leaves and Papete has intermediate green leaves.

5. Pedicels of Ovation Purple are of similar length to Papete (4.5 to 5 cm) but shorter than Harmony Grape (5.5 cm or longer).

6. The pedicels of Ovation Purple are a deeper red-purple color than those of Papete and Harmony Grape.

7. Ovation Purple has a much more mounded growth habit than Papete and Harmony Grape which are more upright.

The accompanying colored photograph illustrates the overall appearance of this cultivar taken as a face view of the plant and showing the colors as true as it is reasonably possible to obtain in a colored reproduction of this type.

The following is a detailed description of my new cultivar, based on plants produced in greenhouses in Lompoc, Calif. during the Fall–Winter season of the year. Plants were grown in 15 cm pots and measurements were taken 20 weeks after rooted cuttings were planted. Height measurements were taken from the soil line of the container. Fertilizer Regime: constant feed; 200 ppm $N_2$, 75 ppm K, 200 ppm P. The plants were grown at 16° C. night temperatures, under 3000 to 4000 foot candles of light and with nutritional trace elements added. Habit of growth, foliage coloration, leaf variegation, size of leaves and flower size will be greatly influenced by nutritional and environmental conditions.

Color references are made to The Royal Horticultural Society Colour Chart except where general terms of ordinary significance are used.

Parentage: A controlled cross between female parent, Papete, U.S. Plant Pat. No. 8,457 and male parent Mikkelsen Seedling No. 92-459-2.

Propagation:

(*A*) *Type cutting*.—Stem tip 15 mm long will develop to 4 to 5 cm long in 18 to 21 days.

(*B*) *Time to root*.—8–10 days at 23° C. summer; 10–12 days at 20° C. winter.

(*C*) *Rooting habit*.—Heavy, fibrous.

Plant description:

(*A*) *Form and habit of growth*.—Mounded to semi-upright, self-branching, intermediate in height, flowers open over the top of leaf canopy; continuous flowering; vigorous growing flowering herb. Average height is 18 to 22 cm and average width is 40 to 45 cm. Internode length is 5 to 6 cm but is highly variable. Pedicel is Greyed-Purple Group 185B, stem is Greyed-Purple Group 185B, and internode is Greyed-Purple Group 185B. Pedicel length is 4.5 cm.

(*B*) *Foliage description*.—Bright green leaves with midrib having reddish cast on lower third of leaf with rest being yellow-green and no leaf variegation. (1) Size: 10 to 11 cm long and 3.5 to 4 cm wide on average mature leaf. (2) Shape: Lanceolate with acuminate apex and acute base. (3) Texture: Both upper and lower surfaces are glabrous. (4) Margin: Finely serrated with fine cilia. (5) Color: Young foliage, top side is Yellow-Green Group 147A, underside is Yellow-Green Group 147B. Mature foliage, top side is Green Group 139A, underside is Yellow-Green Group 147B. (6) Venation: Pinnate, upper side is Yellow-Green Group 146A and lower side is Greyed-Purple Group 185B. (7) Young midrib is Yellow-Green Group 146B with a Greyed-Purple Group 185B cast and mature midrib is Greyed-Purple Group 185B.

(*C*) *Branching*.—The branching is naturally occurring. Lateral branching at base: 5 or more lateral branches. Lateral branch length is 12 to 15 cm but is highly variable.

Flowering description:

(*A*) *Flowering habits*.—Flowers continuously from leaf whorl in a progressively orderly manner with one flower per leaf axil. When the last flower in a whorl opens, the first flower in the leaf whorl above starts to open. It takes 5 to 7 days for a mature but to fully open and the flower may last two weeks or longer depending on the environment. The time to first flower is approximately 8 weeks from root cuttings. The follows are self-cleaning.

(*B*) *Natural flowering season*.—Indeterminate and continuous; quantity of flowering increases with increasing levels of light.

(*C*) *Flower bud*.—Ellipsoidal; flowers perfect; spur is 4.5 cm long. on mature bud, with the throat behind the ovary and originating from the major sepal. Bud length is 16 to 18 mm and bud diameter is 14 mm. Spur is Greyed-Purple Group 185B, spur tip is Greyed-Purple Group 185A, and flower bud is Purple Group 78A just before opening.

(*D*) *Flowers borne*.—On individual red-purple pedicels 4.5 to 5 cm long from a whorl of four to six leaves, more commonly, five. Flowering progressively around the worls as buds and leaves develop. Leaf axils have one flower each.

(*E*) *Quantity of flowers*.—Numerous because of self-branching nature of plant and the long-lasting flower characteristic.

(*F*) *Diameter of flower*.—7.0 to 7.5 cm. Flower Depth: 5 mm.

(*G*) *Petal*.—(1) Shape: Heart; standard petal is largest. (2) Color: Top side in winter when opening is Red-Purple Group 74A; no fading; underside is Purple-Violet Group 80B. (3) Number of petals: Five. (4) Size of petals: Standard: 5.0 cm wide and 3.0 cm long, equal lobes with shallow cut. Wings: 4.0 cm wide and 3.5 cm long, almost equal lobes with moderate cut. Keel: 4.0 cm wide and 3.5 cm long, almost equal lobes with moderate cut.

(*H*) *Reproductive organs*.—(1) Stamens: Five in number. (a) Anther: Hooded shape, color is Yellow-White Group 158B with a Red-Purple Group 74B cast. (b) Pollen color: Yellow-White Group 158C. (2) Pistils: (a) Stigma: Five, segmented column, color is White Group 155B. (b) Style color: Cream. (c) Ovaries: Five in number, size is 6 mm when immature, color is Yellow-Green Group 147A.

(*I*) *Fertility*.—The plants are fertile, but do not normally set seed under greenhouse or garden conditions, unless in a controlled crossing program.

Disease resistance: No significant disease or insect problems seen to date.

OTHER IMPORTANT CHARACTERISTICS

1. Self-branching, early flowering nature allows cultivar to be grown in 10 cm pots but is also very vigorous enough to be grown in 15 to 25 cm containers as well.

2. Minimal fading of older flowers and large overlapping petals result in a round flower that produces an attractive floral display.

3. Has shown the ability to tolerate both high temperatures and full sun and continue to bloom as demonstrated in Connellsville, Pa. summer trials and to bloom as well with cool night temperatures (5 to 10° C.) as demonstrated in outdoor trials in Lompoc, Calif., thus, extending the growing season.

I claim:

1. A new and distinct variety of Impatiens plant named Ovation Purple, as illustrated and described.

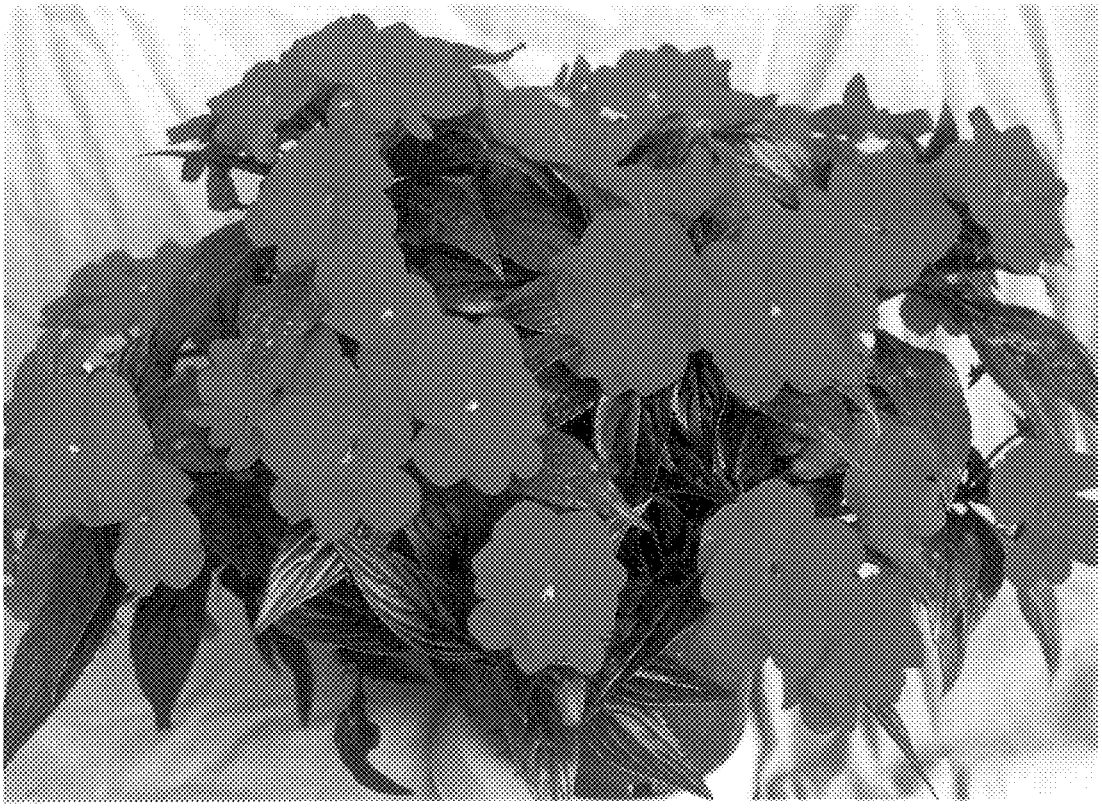

* * * * *